United States Patent [19]
Klopotek

[11] Patent Number: 5,411,501
[45] Date of Patent: May 2, 1995

[54] LASER REPROFILING SYSTEM FOR CORRECTION OF ASTIGMATISMS

[75] Inventor: Peter J. Klopotek, Framingham, Mass.

[73] Assignee: Summit Technology, Inc., Waltham, Mass.

[21] Appl. No.: 72,516

[22] Filed: Jun. 4, 1993

[51] Int. Cl.⁶ .............................................. A61N 5/06
[52] U.S. Cl. .......................................... 606/4; 606/5; 606/11
[58] Field of Search .................. 606/4, 5, 6, 11, 13, 606/17; 219/121.6

[56] References Cited

U.S. PATENT DOCUMENTS

| | | |
|---|---|---|
| 3,262,122 | 7/1966 | Fleisher et al. . |
| 3,558,208 | 1/1971 | Hudson . |
| 3,665,483 | 5/1972 | Becker et al. . |
| 4,139,409 | 2/1979 | Macken et al. . |
| 4,388,517 | 6/1983 | Schulte et al. . |
| 4,414,059 | 11/1983 | Blum et al. . |
| 4,461,294 | 7/1984 | Baron . |
| 4,648,400 | 3/1987 | Schneider et al. . |
| 4,686,979 | 8/1987 | Gruen et al. . |
| 4,732,148 | 3/1988 | L'Esperance, Jr. ............... 606/4 |
| 4,856,513 | 8/1989 | Muller . |
| 4,973,330 | 11/1990 | Azema et al. . |
| 4,994,058 | 2/1991 | Raven et al. ...................... 606/4 |
| 5,019,074 | 5/1991 | Muller . |
| 5,029,220 | 7/1991 | Juday ................................ 606/6 |
| 5,147,352 | 9/1992 | Azema et al. . |

FOREIGN PATENT DOCUMENTS

| | | | |
|---|---|---|---|
| 0224322 | 6/1987 | European Pat. Off. ............ 606/4 |
| 0296982 | 12/1988 | European Pat. Off. ............ 606/5 |
| 0346116 | 12/1989 | European Pat. Off. ............ 606/5 |

OTHER PUBLICATIONS

J. P. Coullahan et al., "Chip Passivation Technique", IBM Technical Disclosure Bulletin, vol. 22, No. 6, Nov. 1979, pp. 2279, 2280, 2281, 285, 2531.

Puliafito et al., "Excimer Laser Ablation of the Cornea and Lens, Experimental Studies", Ophthalmology, vol. 92, No. 6, Jun. 1985, pp. 741–748.

Stephen L. Trokel M.D. et al., "Excimer Laser Surgery of the Cornea", American Journal of Ophthalmology, 1983, 96:710–71.

D. J. O'Hara et al., "Holographic Selective Heating System", IBM Technical Disclosure Bulletin, vol. 11, No. 9, Feb. 1969, pp. 1168–1169.

Primary Examiner—Stephen C. Pellegrino
Assistant Examiner—Sonya C. Harris
Attorney, Agent, or Firm—Thomas J. Engellenner; Mark A. Kurisko; Lahive & Cockfield

[57] ABSTRACT

Apparatus and methods are disclosed for astigmatically ablating surfaces in order to impart new profiles and curvatures to such surfaces. A laser means, e.g., a rapidly pulsed laser radiation source, is aligned with a surface to provide photoablative pulses of energy along an optical path to a target region on the surface. A light restricting means, such as an adjustable iris or profiled mask, is disposed within the optical path to spatially control the extent of the laser radiation striking the target surface. The light restricting means is adapted to permit orientation (e.g., tilting) in various planes relative to the optical path in order to modify the symmetry of the laser beam, e.g., from a circular shape to an elliptical shape, and thereby provide astigmatic ablation of the surface in a single step.

56 Claims, 5 Drawing Sheets

LASER REPROFILING SYSTEM FOR CORRECTION OF ASTIGMATISMS

BACKGROUND OF THE INVENTION

This invention relates generally to methods and apparatus for eroding or ablating surfaces by lasers. In particular, this invention relates to methods and apparatus for ablating surfaces astigmatically, and for the surgical correction of myopic or hyperopic astigmatism through laser keratoplasty, keratomileusis or photorefractive keratectomy (PRK).

It is known to employ laser sources to erode surfaces of workpieces and the like. Such apparatus is in general relatively complex and demands highly skilled use. It is an object of the present invention to provide improved and simplified apparatus and method for eroding surfaces, particularly aspherical surfaces where it is typically desirable to reshape the surface into a more spherical shape having a symmetric and usually uniform curvature.

It is also an object of the present invention to provide an improvement whereby laser techniques can be applied to sensitive surfaces and, in particular, to objects in which it would be undesirable to affect underlying layers. This is particularly important in corneal surgery to correct vision defects, where upper layers of the cornea are sculpted to achieve the proper refractive power. Extreme care must be taken to avoid damage to the basement membrane and the posterior endothelial lining of the cornea in such operations.

In the field of medicine, a known technique for the treatment of certain forms of myopia is surgically to remove a segment of the collagen sub-surface layer of the eye, to reshape the removed segment as by surgical grinding, and to restore the reshaped segment in the eye. The eye heals by reformation of the outer cellular layer over the reshaped collagen layer. Alternatively, a layer of the cornea is opened up as a flap, an artificial or donor lenticular implant is inserted under the flap, and the flap is sutured up again.

It is a further object of this invention to provide an improved and less traumatic method and apparatus for reshaping the cornea of the eye.

Various other surgical techniques for reprofiling of the corneal surface have also been proposed. One increasingly common technique is radial keratotomy in which a set of radial incisions, i.e., resembling the spokes of a wheel, are made in the eye to remedy refractive errors, such as myopia (nearsightedness). As the incisions heal, the curvature of the eye is flattened, thereby increasing the ocular focal distance. The operation is not particularly suitable for correction of astigmatic (non-spherical) conditions and can pose problems, if the surgical incisions are uneven or too deep. Moreover, the results of such relaxing incisions are often hard to predict, especially in the correction of astigmatism.

The use of a laser beam as a surgical tool for cutting incisions, a so-called laser scalpel, has been known for some time (see, for example, U.S. Pat. No. 3,769,963 issued to Goldman et al.). In 1980, a study was made of the damage which might be inflicted on the corneal epithelium by exposure to the recently developed excimer laser (see Taboada et al., "Response of the Corneal Epithelium to ArF excimer laser pulses," *Health Physics* 1981, Volume 40, pp. 677–683). At that period, surgical operations on the cornea were commonly carried out using diamond or steel knives or razor, and further, such techniques were still being studied (see, for example, Binder et al., "Refractive Keratoplasty," *Arch. Ophthalmol.*, May 1982, Vol. 100, p. 802). The use of a physical cutting tool in corneal operations and the insertion of an implant under a flap, continue to be widely practiced up to the present day (see, for example, "Refractive Keratoplasty improves with Polysulfone Pocket Incision," *Ophthalmology Times*, Jul. 1, 1986).

It has been suggested in U.S. Pat. No. 4,665,913 issued to L'Esperance that controlled, ablative, photo-decomposition of one or more selected regions of a cornea can be performed using a scanning action on the cornea with a beam from an excimer laser. Because of the scanning action, it is necessary for L'Esperance to bring his laser beam to a small spot, typically a rounded-square dot of size 0.5 mm by 0.5 mm.

L'Esperance suggests that myopic and hyperopic conditions can be reduced by altering the curvature of the outer surface of the cornea by repeatedly scanning the cornea with an excimer laser beam having this standard, small spot size but varying the field which is scanned during successive scans so that some areas of the cornea are scanned more often than others. In this way, it is claimed, the surface can be eroded by different amounts, depending on the number of times the spot scans the surface. In theory, at least, such scanning systems could be used to replace the shape of an astigmatic cornea with a more spherical shape.

In practice, however, complex apparatus is required to cause a pulsed laser beam to scan with the precision required, if the eroded surface is to be smooth. Thus, in successive sweeps of a scan overlap, there will be excessive erosion in the overlap area, whereas, if they fail to meet, a ridge will be left between the sweeps. The pulsed nature of excimer laser radiation also tends to exacerbate this problem. Additionally, the scanning method is inherently time-consuming even with highly refined techniques and apparatus, since the laser beam is only eroding a very small part of the total area to be treated at any given moment. Furthermore, such a scanning system can cause rippling effects on relatively soft materials, such as corneal tissue.

Another technique for corneal reshaping involves the use of a laser photoablation apparatus in which the size of the area on the surface to which the pulses of laser energy are applied is varied to control the reprofiling operation. In one preferred embodiment, a beam-shaping stop or window is moved axially along the beam to increase or decrease the region of cornea on which the laser radiation is incident. By progressively varying the size of the exposed region, a desired photoablation profile is established in the surface. For further details on this technique, see also Marshall et al., "Photo-ablative Reprofiling of the Cornea Using an Excimer Laser: Photorefractive Keratectomy," Vol. 1, *Lasers in Ophthalmology*, pp. 21–48 (1986), and U.S. Pat. No. 4,941,093 issued to Marshall et al., both of which are herein incorporated by reference.

Although this technique for varying the size of the exposed region is a substantial improvement over physical shaping (i.e., scalpel) techniques and laser spot scanning protocols, correction of astigmatic conditions is difficult. An astigmatic surface is typically defined by two natural and orthogonal curvatures which form the surface. A varying circular spot size will create or remove a single power (e.g., flatten or steepen the curvature relative to a point, the center of the optical axis).

To correct astigmatism, U.S. Pat. No. 4,941,093 teaches the use of specially configured optical elements or slits to provide ablation in one axis, i.e., such that the erosion proceeds selectively relative to a line rather than around a point. Typically, this approach requires a second step to provide spherical correction so that the proper overall curvature is achieved. In this approach, proper selection and precise superposition of two ablation patterns is necessary.

Yet another approach involves the use of a graded intensity laser beam or a graded absorption/transmission mask or a photodecomposable mask which varies the transmission of ablative laser radiation to the target surface, thereby inducing variable ablative depths on the surface. For example, U.S. Pat. No. 4,856,513 entitled "Laser Reprofiling Systems And Methods" which describes methodology for selectively eroding the cornea through the use of an erodable mask. The mask absorbs the surface laser radiation in varying amounts across the corneal surface to provide the desired surface profiles. This technique though requires the manufacture of a complementary object, i.e., the erodable mask, which compensates for the astigmatism and also requires precise correlative alignment with the axes of the target surface.

It is, accordingly, an object of this invention to provide a simpler method and apparatus for astigmatically reprofiling a surface with an initial, bi-powered, astigmatic shape in order to achieve a new, preferably spherical, shape.

It is another object of this invention to provide a method and apparatus for orienting and adjusting the astigmatic ratio applied to a surface shape with increased control.

It is further an object of this invention to provide a method and apparatus for correcting myopic astigmatism through corneal ablation in laser keratoplasty, keratomileusis or other PRK-type procedures.

These and other objects of the invention are evident in the description that follows.

SUMMARY OF THE INVENTION

Apparatus and methods are disclosed for astigmatically ablating surfaces in order to impart new profiles and curvatures to such surfaces. A laser means, e.g., a rapidly pulsed laser radiation source, is aligned with a surface to provide photoablative pulses of energy along an optical path to a target region on the surface. A light restricting means, such as an adjustable iris or profiled mask, is disposed within the optical path to spatially control the extent of the laser radiation striking the target surface. The light restricting means is adapted to permit orientation (e.g., tilting) in various planes relative to the optical path in order to modify the symmetry of the laser beam, e.g., from a circular shape to an elliptical shape and thereby provide astigmatic ablation of the surface in a single step.

In a simple embodiment of the invention, a laser system is disclosed having a series of elements. These elements include a light restricting means, an orientation means and an imaging means. The light restricting means can employ an adjustable iris or a profiled mask to vary the size of a laser beam over time. The term "adjustable iris" is used herein to encompass various systems from modifying the physical size or orientation of laser beam, as well as the spatial and temporal allocation of such a laser beam, including, for example, adjustable diaphragms, aperture wheels, movable stops and other mechanisms, as well as optical elements associated therewith to maintain beam homogeneity. The term "profiled mask" as used herein is intended to encompass various light restricting media which rely upon physical properties of a mask element to absorb and/or selectively transmit radiation over time, including, for example, graded intensity masks, photodecomposable masks, photobleachable masks, and erodable masks, as well as optical elements associated therewith to maintain beam homogeneity. The imaging means encompasses one or more lens, mirrors or combinations thereof which serve to image the aperture (or equivalent spatial location in the case of a profiled mask) onto an image plane at the surface to be reprofiled. The term "asymmetric" ablation as used herein is intended to encompass various ablation profiles that achieve the correction of astigmatic errors in surface geometry.

The orientation means is preferably adapted to permit rotation of the light restricting means in two dimensions relative to the beam path (referred to herein as the "$\alpha$" and "$\beta$" directions). In one illustrated embodiment, the orientation means employs a gimbal mechanism to permit tilting in either or both angular directions. The tilting of the light restricting means relative to the laser beam path causes an elliptical exposure pattern of laser energy to be imaged at the target surface. By appropriate selection of the orientation, the astigmatic erosion axis and erosion ratio is defined. In simple terms, the more elongated the elliptical or otherwise asymmetric pattern, the greater the astigmatic ratio will be.

The advantages presented by the features and aspects of this invention are several. In particular, the invention provides for an elliptical irradiation pattern to a target surface, enabling simultaneous and bi-powered astigmatic ablation. The orientation means allows for easy polar orientation and selection of the astigmatic ablation pattern. Applications, such as excimer laser keratoplasty, can take full advantage of this invention by ensuring proper axial orientation of the astigmatic correction applied to the myopic cornea. Furthermore, various astigmatic ratios can be achieved. The normal keratoplasty procedures can then be followed by adjusting the light restricting means to achieve the desired optical correction of the cornea.

The invention will next be described in connection with certain illustrated embodiments: however, it should be clear that various additions, subtractions and modifications can be made by those skilled in the art without departing from the spirit or scope of the invention. For example, the invention can be used in connection with congenital or other host-operative (e.g., cataract or penetrating keratoplasty) astigmatisms. Similarly, the invention can be used with prior art techniques in which a segment of the cornea is removed, reshaped, and then reimplanted into the cornea, as well as with donor lenticular implants. In such cases the excised segment or donor implants can be reprofiled in accordance with the invention to yield astigmatic corrections. The invention can also be used in conjunction with various auxiliary components which monitor and/or control the procedure, including, for example, various feed back control systems for modifying the orientation means on the laser.

BRIEF DESCRIPTION OF THE DRAWINGS

A more complete understanding of the invention may be obtained by reference to the drawings in which.

DETAILED DESCRIPTION

Figure 1:
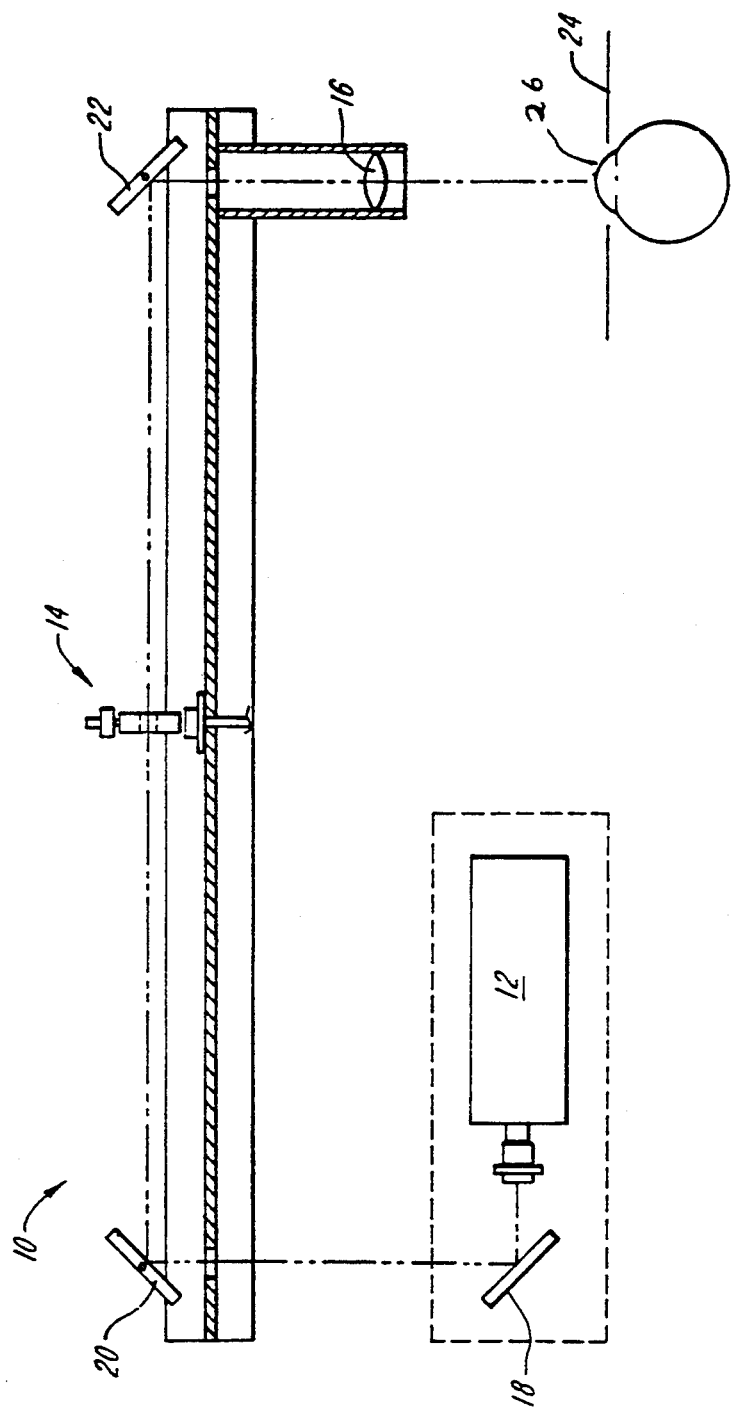
FIG. 1 is a diagrammatic illustration of apparatus for practicing a method of ablating a target surface astigmatically, in accordance with the invention.

FIG. 1 illustrates a system 10 according to the invention for delivering an elliptical beam of ablative laser energy to a target surface. In FIG. 1, system 10 includes laser 12, light restricting assembly 14, and imaging assembly 16 in optical alignment to transmit a beam of ablative laser energy to an image plane 24 on a surface, such as the cornea 26 of an eye. Mirrors 18, 20 and 22 permit the system to operate in a folded configuration. The laser 12 can provide continuous or pulsed laser radiation output to the light restricting assembly 14.

Figure 2:
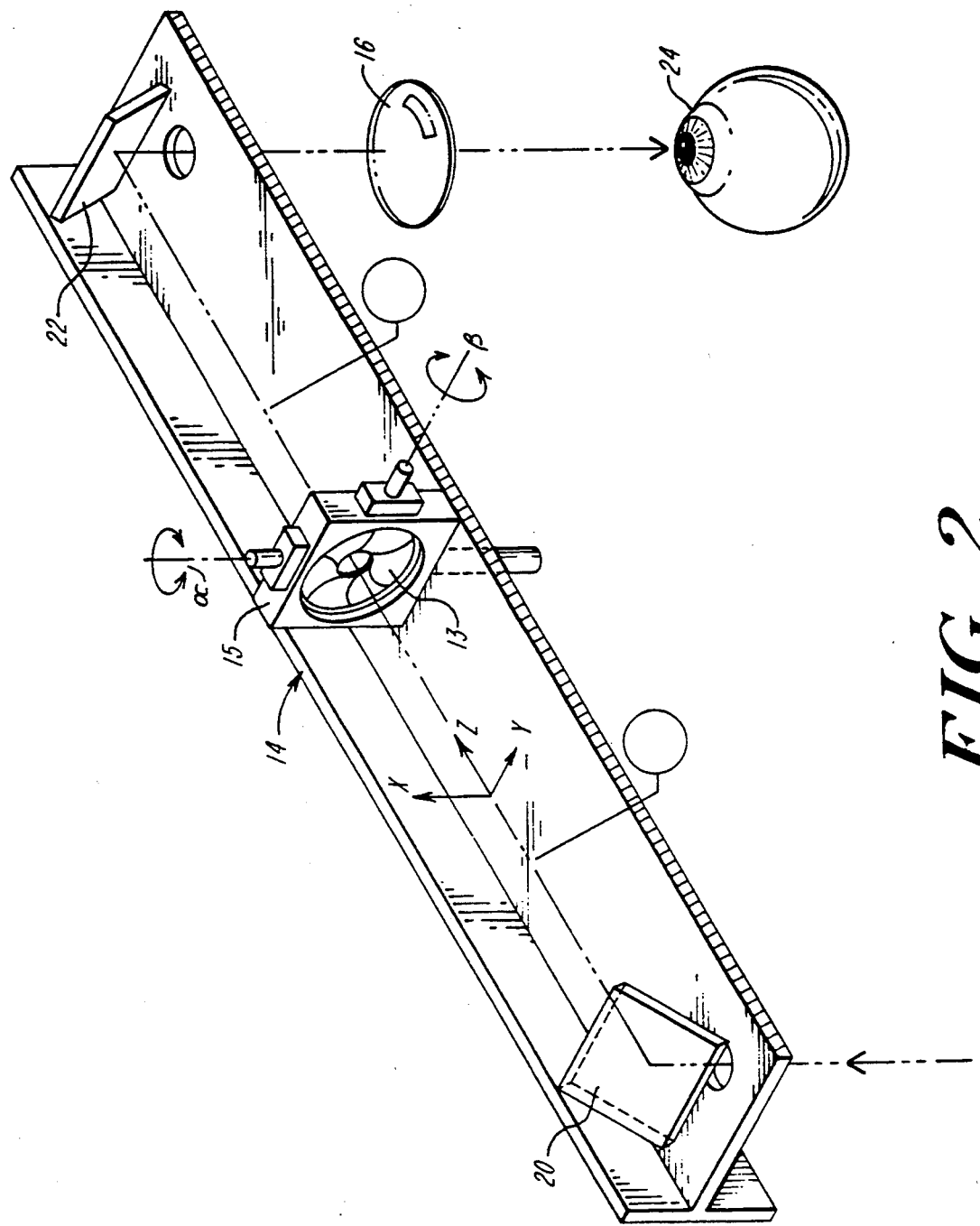
FIG. 2 is a schematic perspective view of the optical elements of the system of FIG. 1 configured to effect a conventional, time-varying, circular exposure area on the surface of a cornea.

As shown in more detail in FIG. 2, the light restricting assembly 14 can include an adjustable iris 13 and a gimbal mechanism 15 to permit rotation in both the $\alpha$ and $\beta$ angular directions. The optical assemblies 14 and 16 are coaxially aligned with the laser 12 so as to provide optimal and unaberrated throughput to the target surface 24. (The assembly of optical elements shown in FIGS. 2–4 can be augmented by additional beam-shaping or beam controlling elements, known to those skilled in the art, such as beam clipping mechanisms, light homogenizers and/or beam expanders. For purposes of simplified illustration, these elements have been omited from the drawing.)

The adjustable iris 13 provides a mechanism for varying the beam width over time. When the light restricting means in oriented in the null position (as shown in FIG. 2), and the iris is slowly opened, a series of circular exposure patterns will be transmitted to the surface and providing cumulative exposure of the greatest duration for those regions of the surface located on or near the optical axis. In contrast, those regions further away from the optical axis will receive less ablative radiation. The net effect is a flattening of the curvature. The null position illustrated in FIG. 2 would be preferred for procedures involving a spherical surface having a smaller than desired radius of curvature (a e.g., myopic, but non-astigmatic, eye).

It should be clear that various other light restricting means also can be employed in lieu of the adjustable iris 13 to vary the flux density delivered to the target over time. For example, graded intensity masks, photoerodable masks or photobleachable masks can be used. Additionally, masks of various geometric designs can be rotated or otherwise manipulated to yield a time-varying, exposure pattern.

Figure 3:
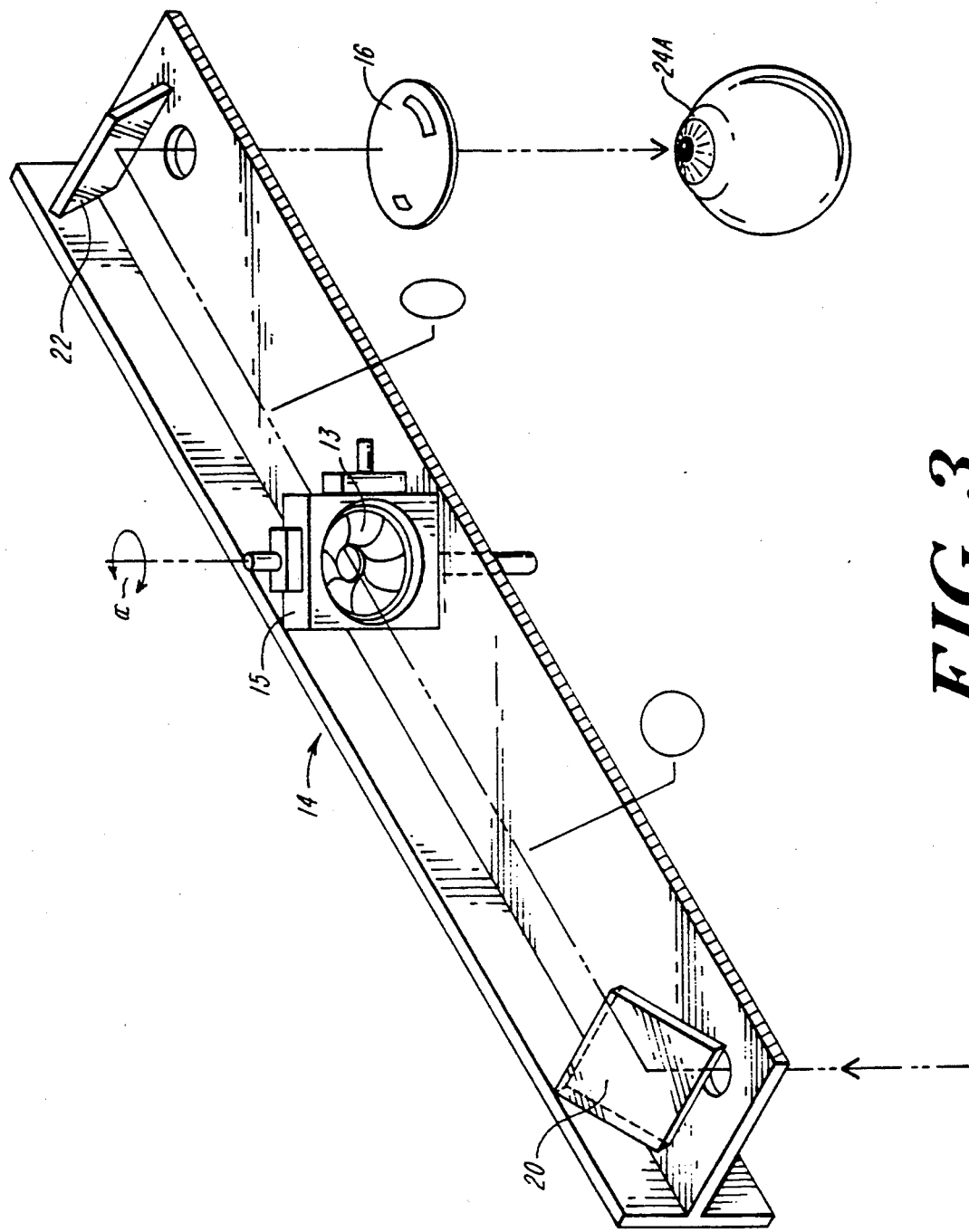
FIG. 3 is a schematic perspective view of another configuration of the optical elements of the system of FIG. 1 in which the aperture is tilted in one direction relative to the beam path to effect an time-varying, elliptical exposure area on the surface of a cornea.
Figure 4:
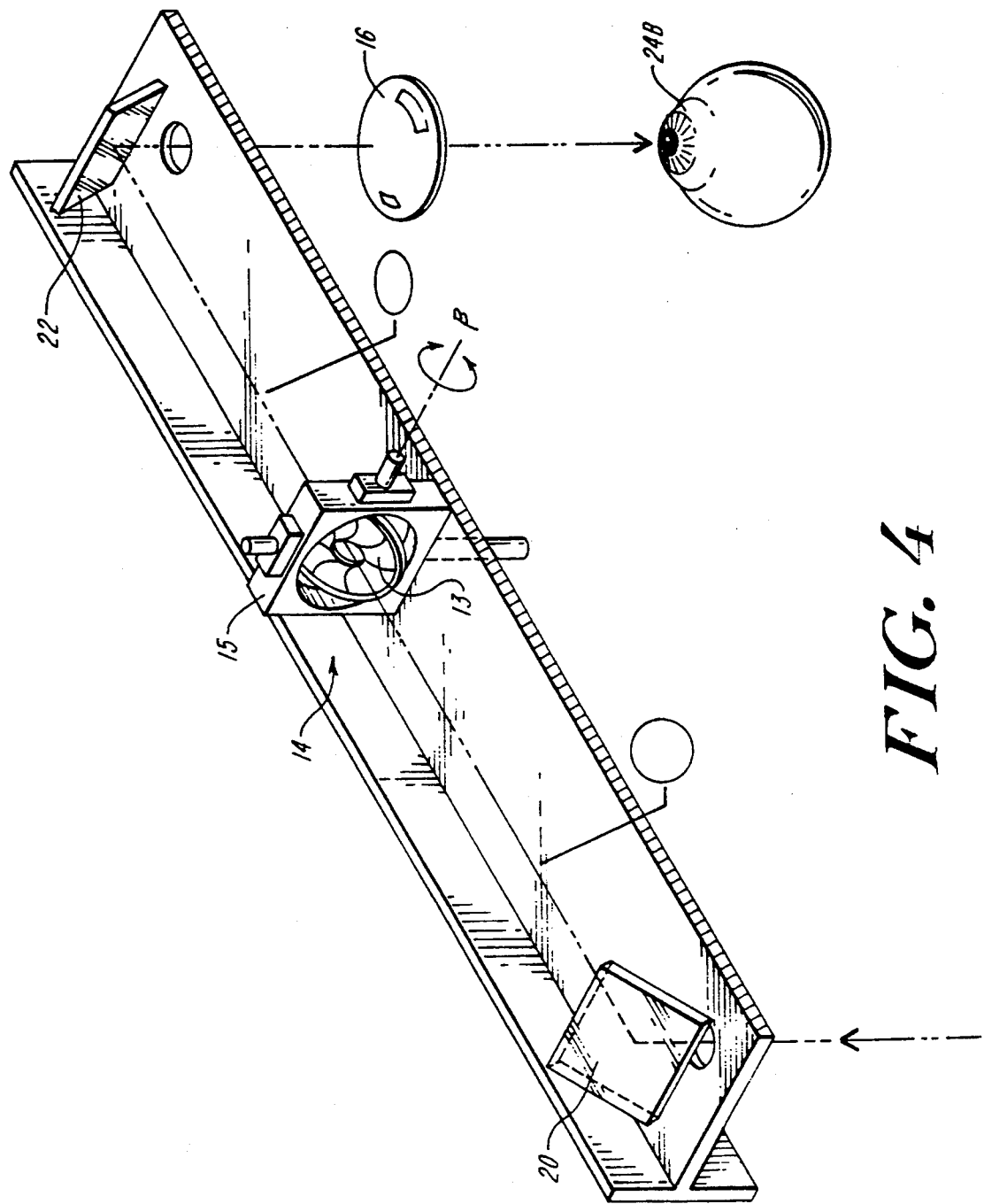
FIG. 4 is a schematic perspective view of a further configuration of the optical elements of the system of FIG. 1 in which the aperture is tilted to a different degree in another direction relative to the beam path to effect an time-varying, elliptical exposure area of different shape and orientation on the surface of a cornea.

When the light restricting assembly is tilted, as shown in FIGS. 3 and 4, elliptical beam patterns are transmitted to the eye. The adjustable iris 13 modifies the size of the elliptical pattern, while the orientation of the aperture relative to the beam path will define the orientation of the major and minor axes of the ellipse. In this simple manner, an astigmatic ablation pattern which modifies the surface can be created and fitted to compensate for the particular orientation and degree of astigmatism presented by the target surface.

In particular, the system depicted in FIGS. 1–4 illustrates a methology for performing excimer laser keratomileusis. Laser means 12 is a rapidly pulsed UV laser source, and the target surface 24 is the human cornea, optically aligned to the laser means 12. The laser means, for example, can be an excimer laser, and one preferred laser is an Argon-Fluoride laser having a characteristic emission wavelength of about 193 nanometers. Alternatively, other pulsed UV lasers having both shorter wavelengths down to about 157 nm (e.g., a Fluoride laser) and longer wavelengths up to about 300 nm may be useful in particular applications.

For example, in the case of ablating either Bowman's membrane or the stromal portion of the cornea by energy of wavelength 193 nm (the wavelength obtained from an ArF Excimer laser), the threshold value is about 50 mJ per $cm^2$ per pulse, and the saturation value is about 250 mJ per $cm^2$ per pulse. Suitable energy densities at the corneal surface are 50 mJ per $cm^2$ to one J per $cm^2$ per pulse for a wavelength of 193 nm.

The threshold value can vary very rapidly with wavelength, and at 157 nm, which is the wavelength obtained from an $F_2$ laser, the threshold is about 5 mJ per $cm^2$ per pulse. At this wavelength, suitable energy densities at the corneal surface are 5 mJ per $cm^2$ to one J per $cm^2$ per pulse.

Most preferably, the laser system is used to provide an energy density at the surface to be eroded of slightly less than the saturation value. Thus, when eroding the cornea with a wavelength of 193 nm (under which conditions the saturation value is 250 mJ per $cm^2$ per pulse), it is preferable to provide to the cornea pulses of an energy density of 90 to 220 mJ per $cm^2$ per pulse. Typically, a single pulse will erode a depth in the range 0.1 to 1 micrometer of collagen from the cornea.

The pulse repetition rate for the laser may be chosen to meet the needs of each particular application. Normally, the rate will be between 1 and 500 pulses per second, preferably between 1 and 100 pulses per second. When it is desired to vary the beam size, the laser pulses may be stopped. Alternatively, the beam size may be varied while the pulses continue. If a measurement device is used to monitor the erosion progress and control the laser system automatically, the beam size may be varied continuously at a controlled rate without interrupting the pulses.

Suitable irradiation intensities vary depending on the wavelength of the laser, and the nature of the irradiated object. For any given wavelength of laser energy applied to any given material, there will typically be a threshold value of energy density below which significant erosion does not occur. Above the threshold density, there will be a range of energy densities over which increasing energy densities give increasing depths of erosion until a saturation value is reached. For increases in energy density above the saturation value, no significant increase in erosion occurs.

The threshold value and the saturation value vary from wavelength to wavelength of laser energy and from material to material of the surface to be eroded, in a manner which is not easily predictable. However, for any particular laser and any particular material, the values can be found readily by experiment.

With reference to FIGS. 3 and 4, the patient's astigmatic axis can be fit to the elliptical beam profile through the orientation of the light restricting iris 14. The apertures of the adjustable iris will control one dimension of the ellipse at the corneal target surface 24A or 24B. Rotating the aperture relative to the beam path (i.e., tilting the light restricting means 14, via gimbal assembly 15) through an angle $\alpha$ (as shown in FIG. 3) or an angle $\beta$ (as shown in FIG. 4), or through a composite angle will control the other dimension (and orientation on the surface) of the ellipse.

Although the invention has been described for sake of illustration in terms of simple rotation of the light restricting means 14 about the x axis (angle $\alpha$) or about the y axis (angle $\beta$), or both, it should be clear that other coordinate systems also can be used to describe the astigmatic correction process. For example, a spherical coordinate system can be employed to describe the astigmatic axis of the eye (or a complementary astigmatic correction axis). In such a system, one angle (e.g., "$\theta$") can describe the orientation of the axis of the astigmatic correction on the eye (i.e., in the x-y plane), and another angle (e.g., "$\phi$") can define the proportion of the major-to-minor axis. The conversion of angles from one coordinate system to another is governed by well-known geometric equations.

It is also preferable that the system 10 produce an output beam having a substantially constant energy per unit area regardless of its varying size. For further details on basic laser keratomileusis systems and methods, as well as techniques for ensuring substantial constant energy density, see U.S. Pat. Nos. 4,941,093 and 4,856,516, both of which are incorporated herein by reference.

The rate of change in the size of the elliptical exposure area depends upon the selected radius of curvature for the surface erosion. For one dimension, the power of a surface can be described in terms of Diopters (1/meter units), the typical terminology for vision correction. A Diopter is defined as $$\text{Diopter} = \frac{n' - n}{R}$$

where n and n' are the wavelength dependent optical indexes of refraction before and within target surface 24, respectively. R is the radius of the surface. In excimer laser keratoplasty or keratomileusis procedures, the index n of the incident medium is air, with an index of approximately 1. The index of the average human cornea, n', is approximately 1.376 for visible light. If a patient needs a $-3.0$ Diopter correction, the radius of the surface erosion is about 125.33 mm. The successive irradiations on the cornea are, therefore, adjusted in size to erode the corneal surface to that radius.

If a patient has myopic astigmatism, or more commonly called astigmatic near-sightedness, both axes of the cornea can be eroded simultaneously to perform a bi-powered erosion. If, for example, a $-3.0$ Diopter correction is needed in one axis and a $-3.9$ Diopter correction is needed in the orthogonal axis on the cornea, the corresponding irradiation size of the elliptical excimer laser beam is about 4.6 mm and 4.0 mm, respectively. The thickness t of the cornea removed during the ablation will vary depending upon size of the optical zone being reprofiled. The procedure can be largely confined to erosion of the Bowman's layer of the cornea, if desired, by choosing a small, optical zone for reprofiling. Alternatively, a larger optical zone may be desired and, in such case, penetration into the stromal region of the cornea will typically occur. Generally, it is desirable to avoid ablation of more than 100–200 microns of the cornea, in any event.

Figure 5A:
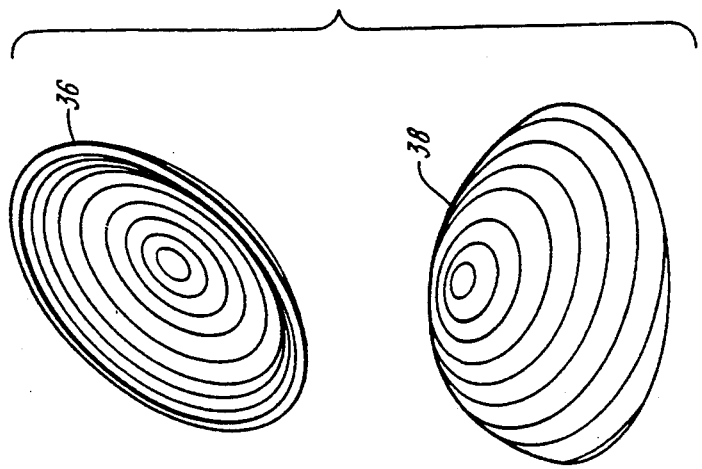
FIG. 5A illustrates diagrammatically the use of a spherical ablation mask on a simple myopic cornea as an alternative to an adjustable aperture.
Figure 5B:
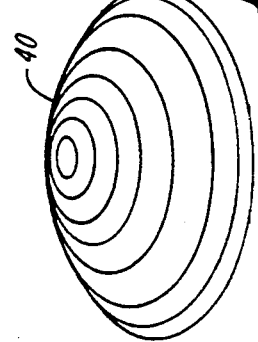
FIG. 5B illustrates the shape of the cornea following the procedure illustrated in FIG. 5A.

FIGS. 5A–5B and 6A–6B illustrate the effects of astigmatic ablation on a myopic astigmatic eye using an alternative light restriction means, a profiled mask 36. FIG. 5A illustrates diagrammatically the use of a spherical ablation mask on a simple myopic cornea as an alternative to an adjustable aperture. In this approach, described in more detailed in U.S. Pat. No. 4,856,513, herein incorporated by reference, the profiled mask 30 selectively blocks more of the radiation at the periphery of the laser beam and transmits more radiation to those regions of the myopic eye 32 located at or near the optical axis. The net results shown in FIG. 5B is a flatten curvature 34 on the surface of the eye. In this fashion, the profiled mask in 32 selectively ablates the corneal surface and provides a correct curvature for normal vision.

Figure 6A:
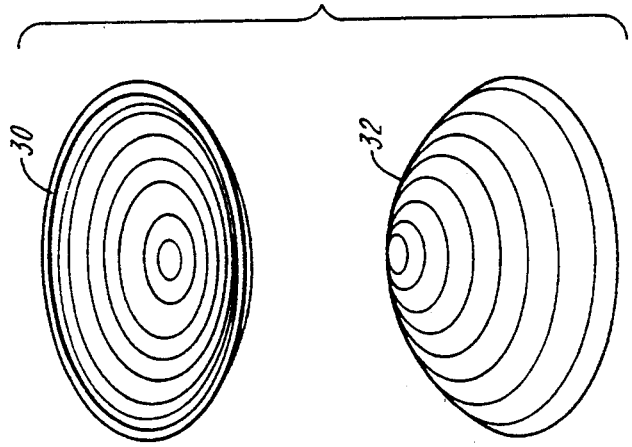
FIG. 6A illustrates diagrammatically the use of a tilted, spherical ablation mask on an astigmatic myopic cornea.
Figure 6B:
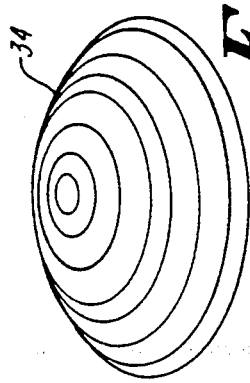
FIG. 6B illustrates the shape of the cornea following the procedure illustrated in FIG. 6A.

The use of a similar spherical ablation mask 36 on a myopic astigmatic eye 38 is shown in FIG. 6A. By tilting the mask relative to the optical axis, an elliptical exposure pattern is again created in a manner similar to that described above with the adjustable iris in connection with FIGS. 1-4. Once more, the net result is a corrected curvature 40 which is no longer astigmatic or myopic, as shown in FIG. 6B.

The degree of astigmatic correction will, of course, vary with the tilt of the aperture or mask in accordance with geometric and optical principles. Essentially, the degree of tilting will compound the ablative effects (and therefore, the correction factor because the beam will effect a smaller diameter of the eye. For example, if the adjustable is tilted 60 degrees in the D direction, the magnitude of the ablative effects will be about twice as great along the major (tilt) axis (e.g., a 2 diopter change in the minor axis will be accompanied by a 4 diopter change along the tilt axis).

In the general case, when the surface of an eye is astigmatic and has two orthogonal axes, the degree of astigmatism can be characterized by two values, $D_1$ and $D_2$, which represent the smaller and larger dioptric corrections necessary along these two axes, respectively. To perform the correction with an ablative procedure, the following equation can be employed:

$$(DIA_1)^2 D_1 = (DIA_2)^2 D_2 \tag{1}$$

where $DIA_1$ and $DIA_2$ are the diameters of the ablative ellipsoid on the two elliptical axes. To perform a procedure according to the invention, the tilt of the iris in the spherical coordination system (i.e., at an angle $-\phi$ from the Z axis) can be determined by the following equation.

$$\phi = \arccos \sqrt{D_1/D_2} \qquad (2)$$

When a mask is used instead of an aperture, a modification of equation (2) is typically desired to take into account the global decrease in erosion rate due to the decrease in density of photons striking the mask material. These correction factors can be determined empirically by those skilled in the art and may vary based on the composition and type of mask employed.

It should also be appreciated that distortions due to "depth of field" effects should be minimized. For aperture systems, this can be achieved through the use of a low numerical aperture less downstream of the light restricting means (e.g., lens 16 as shown in FIGS. 1-4 or similar multi-element lens systems). The "depth of field" effect can also be minimized by insuring that the beam of light passing through the light restricting means is composed of essential parallel light rays. Increased depth of field can also be achieved by placing a field lens in the vicinity of a light restricting aperture. The parallel light approach is particularly useful with erodable mask embodiments and the like.

The invention has been described in connection with illustrated embodiments. However, it should be clear that various other alternative embodiments can be constructed in which the principles disclosed herein are implemented, in particular by the use of light restricting means to break the symmetry of the laser beam and thereby provide a time varying, astigmatic energy distribution to the surface undergoing ablation.

What is claimed is:

1. A method for ablating a surface astigmatically by laser energy, the method comprising the steps of:
    aligning a surface with a laser means, which is operable to deliver a beam of photoablative pulses of laser energy along a path to the surface where the beam forms an exposure area on the surface;
    disposing a light restricting means within the beam path for selectively transmitting the laser energy and for varying the exposure area on the surface over time; and
    orienting the light restricting means at a non-perpendicular angle relative to the beam path to create an elliptical output beam and define an asymmetric ablation profile.

2. The method of claim 1 wherein the step of orienting the light restricting means further comprises forming a time-varying, astigmatic distribution of energy on said exposure area.

3. The method of claim 1 wherein the step of orienting the light restricting means further comprises tilting the light restricting means off a normal plane in at least one angular direction relative to the beam path to select a particular orientation for the asymmetric ablation profile.

4. The method of claim 3 wherein the step of tilting the light restricting means further comprises forming a time-varying, elliptical distribution of energy on said area in which the angular direction defines first and second orthogonal axes on said surface for astigmatic ablation.

5. The method of claim 4 wherein the method further includes the step of adjusting the tilt of the light restricting means to define a ratio of a major axis to a minor axis of the elliptical distribution of energy which compensates for a particular degree of astigmatism.

6. The method of claim 1 wherein the step of disposing a light restricting means within the beam path further comprises the step of disposing an adjustable iris within the beam path.

7. The method of claim 1 wherein the step of disposing a light restricting means within the beam path further comprises the step of disposing a profiled mask within the beam path.

8. The method of claim 7 wherein the step of disposing a profiled mask within the beam path further comprises the step of disposing a laser ablatable mask within the beam path.

9. The method of claim 1 further comprising the steps of activating the laser means to generate ablative radiation and activating the light restricting means to selectively ablate the surface by changing the size of the exposure area over time.

10. The method of claim 9 wherein the step of activating the laser means further comprises the step of activating a pulsed excimer laser means.

11. A method for providing astigmatic ablation to an area of the cornea of an eye for correcting myopic astigmatism, the method comprising the steps of:
    aligning a corneal surface with a laser means, which is operable to deliver a beam of photoablative pulses of laser energy along a path to the surface where the beam forms an exposure area on the surface;
    disposing a light restricting means within the beam path for selectively transmitting the laser light and for varying the exposure area on the corneal surface over time; and
    orienting the light restricting means at a non-perpendicular angle relative to the beam path to create an elliptical output beam and define an asymmetric ablation profile.

12. The method of claim 11 wherein the step of orienting the light restricting means further comprises the step of forming a time-varying, astigmatic distribution of energy on said exposure area.

13. The method of claim 11 further comprising the step of tilting the light restricting means off a normal plane in at least one angular direction relative to the beam path to select a particular orientation for the asymmetric ablation profile.

14. The method of claim 13 wherein the step of tilting the light restricting means further comprises the step of forming a time-varying, elliptical distribution of energy on said area in which the angular direction defines first and second orthogonal axes on said surface for astigmatic ablation.

15. The method of claim 14 wherein the method further includes the step of adjusting the tilt of the light restricting means to define a ratio between a major axis and a minor axis of the elliptical distribution of energy which compensates for a particular degree of astigmatism.

16. The method of claim 11 wherein the step of disposing a light restricting means within the beam path further comprises the step of disposing an adjustable iris within the beam path.

17. The method of claim 11 wherein the step of disposing a light restricting means within the beam path further comprises the step of disposing a profiled mask within the beam path.

18. The method of claim 17 wherein the step of disposing a profiled mask within the beam path further comprises the step of disposing a laser ablatable mask within the beam path.

19. The method of claim 11 wherein the method further comprises the steps of activating the laser means to generate ablative radiation and activating the light restricting means to selectively ablate the surface by changing the size of the exposure area over time.

20. The method of claim 19 wherein the step of activating the laser means further comprises the step of activating a pulsed excimer laser means.

21. A laser system for astigmatically reprofiling a surface, said laser system comprising:
   laser means for generating pulses of laser light along a beam path at an energy level such that the pulses can be absorbed at a surface to induce photoablation and such that the laser light forms an exposure area on the surface;
   light restricting means disposed within the beam path for selectively transmitting the laser light and for varying the exposure area on the surface over time; and
   orientation means for orienting the light restricting means at a non-perpendicular angle relative to the beam path to create an elliptical output beam and define an asymmetric ablation profile.

22. A laser system according to claim 21 wherein the laser means comprises an excimer laser.

23. A laser system according to claim 22 wherein the excimer laser is an Argon-Fluoride laser.

24. A laser system according to claim 21 wherein said beam has a diameter and wherein said light restricting means comprises an adjustable iris for varying the diameter.

25. A laser system according to claim 21 wherein said beam has a diameter and wherein said light restricting means comprises a profiled mask for varying the diameter.

26. A laser system according to claim 25 wherein the profiled mask is a laser ablatable mask.

27. A laser system according to claim 21 wherein said orientation means further comprises a gimbal mount which permits the light restricting means to be tilted at various angles relative to the beam path to select a particular orientation for the asymmetric ablation profile.

28. A laser system according to claim 21 wherein the system further comprises imaging means for imaging the light restricting means onto an image plane at the surface.

29. A method for ablating a surface astigmatically by laser energy, the method comprising the steps of:
   aligning a surface with a laser means, which is operable to deliver a beam of photoablative pulses of laser energy along a path to the surface where the beam forms an exposure area on the surface;
   disposing a light restricting means within the beam path for selectively transmitting the laser energy and for varying the exposure area on the surface over time; and
   orienting the light restricting means at a variable angle relative to the beam path to define an asymmetric ablation profile.

30. The method of claim 29 wherein the step of orienting the light restricting means further comprises forming a time-varying, astigmatic distribution of energy on said exposure area.

31. The method of claim 29 wherein the step of orienting the light restricting means further comprises tilting the light restricting means off a normal plane in at least one angular direction relative to the beam path to select a particular orientation for the asymmetric ablation profile.

32. The method of claim 31 wherein the step of tilting the light restricting means further comprises forming a time-varying, elliptical distribution of energy on said area in which the angular direction defines first and second orthogonal axes on said surface for astigmatic ablation.

33. The method of claim 32 wherein the method further includes the step of adjusting the tilt of the light restricting means to define a ratio between a major axis and a minor axis of the elliptical distribution of energy which compensates for a particular degree of astigmatism.

34. The method of claim 29 wherein the step of disposing a light restricting means within the beam path further comprises the step of disposing an adjustable iris within the beam path.

35. The method of claim 29 wherein the step of disposing a light restricting means within the beam path further comprises the step of disposing a profiled mask within the beam path.

36. The method of claim 35 wherein the step of disposing a profiled mask within the beam path further comprises the step of disposing a laser ablatable mask within the beam path.

37. The method of claim 29 further comprising the steps of activating the laser means to generate ablative radiation and activating the light restricting means to selectively ablate the surface by changing the size of the exposure area over time.

38. The method of claim 37 wherein the step of activating the laser means further comprises the step of activating a pulsed excimer laser means.

39. A method for providing astigmatic ablation to an area of the cornea of an eye for correcting myopic astigmatism, the method comprising the steps of:
   aligning a corneal surface with a laser means, which is operable to deliver a beam of photoablative pulses of laser energy along a path to the surface where the beam forms an exposure area on the surface;
   disposing a light restricting means within the beam path for selectively transmitting the laser light and for varying the exposure area on the corneal surface over time; and
   orienting the light restricting means at a non-perpendicular angle relative to the beam path to create an elliptical output beam and define an asymmetric ablation profile.

40. The method of claim 39 wherein the step of orienting the light restricting means further comprises the step of forming a time-varying, astigmatic distribution of energy on said exposure area.

41. The method of claim 39 further comprising the step of tilting the light restricting means off a normal plane in at least one angular direction relative to the beam path to select a particular orientation for the asymmetric ablation profile.

42. The method of claim 41 wherein the step of tilting the light restricting means further comprises the step of forming a time-varying, elliptical distribution of energy on said area in which the angular direction defines first and second orthogonal axes on said surface for astigmatic ablation.

43. The method of claim 42 wherein the method further includes the step of adjusting the tilt of the light restricting means to define a ratio between a major axis and a minor axis of the elliptical distribution of energy which compensates for a particular degree of astigmatism.

44. The method of claim 39 wherein the step of disposing a light restricting means within the beam path further comprises the step of disposing an adjustable iris within the beam path.

45. The method of claim 39 wherein the step of disposing a light restricting means within the beam path further comprises the step of disposing a profiled mask within the beam path.

46. The method of claim 45 wherein the step of disposing a profiled mask within the beam path further comprises the step of disposing a laser ablatable mask within the beam path.

47. The method of claim 39 wherein the method further comprises the steps of activating the laser means to generate ablative radiation and activating the light restricting means to selectively ablate the surface by changing the size of the exposure area over time.

48. The method of claim 47 wherein the step of activating the laser means further comprises the step of activating a pulsed excimer laser means.

49. A laser system for astigmatically reprofiling a surface, said laser system comprising:

laser means for generating pulses of laser light along a beam path at an energy level such that the pulses can be absorbed at a surface to induce photoablation and such that the laser light forms an exposure area on the surface;

light restricting means disposed within the beam path for selectively transmitting the laser light and for varying the exposure area on the surface over time; and variable orientation means for orienting the light restricting means at a variable angle relative to the beam path to define an asymmetric ablation profile.

50. A laser system according to claim 49 wherein the laser means comprises an excimer laser.

51. A laser system according to claim 50 wherein the excimer laser is an Argon-Fluoride laser.

52. A laser system according to claim 49 wherein said beam has a diameter and wherein said light restricting means comprises an adjustable iris for varying the diameter.

53. A laser system according to claim 49 wherein said beam has a diameter and wherein said light restricting means comprises a profiled mask for varying the diameter.

54. A laser system according to claim 53 wherein the profiled mask is a laser ablatable mask.

55. A laser system according to claim 49 wherein said orientation means further comprises a gimbal mount which permits the light restricting means to be tilted at various angles relative to the beam path to select a particular orientation for the asymmetric ablation profile.

56. A laser system according to claim 49 wherein the system further comprises imaging means for imaging the light restricting means onto an image plane at the surface.

* * * * *